United States Patent [19]

Logan

[11] 4,185,027

[45] Jan. 22, 1980

[54] HYDROLYSIS OF METHYL ESTERS

[75] Inventor: Ted J. Logan, Cincinnati, Ohio

[73] Assignee: The Procter & Gamble Company, Cincinnati, Ohio

[21] Appl. No.: 915,855

[22] Filed: Jun. 15, 1978

[51] Int. Cl.$^2$ ............................ C11C 1/04; C11C 1/00
[52] U.S. Cl. .................................... 260/415; 260/413; 260/416; 562/598; 562/606
[58] Field of Search ................... 260/413 R, 415, 416; 562/598, 606

[56] References Cited

U.S. PATENT DOCUMENTS

| 1,558,299 | 4/1922 | Schwartz | 260/410.7 |
| 1,882,808 | 10/1932 | Graves | 260/413 R |

OTHER PUBLICATIONS

Gault et al., Comptes Rendus, vol. 207, pp. 293–295 (1938).
Gault et al., Comptes Rendus, vol. 203, pp. 729–731, (1936).
Meade et al., JAOCS, vol. 39, pp. 1–6, 1962.

*Primary Examiner*—John F. Niebling
*Attorney, Agent, or Firm*—Ronald L. Hemingway; Richard C. Witte

[57] ABSTRACT

A process for hydrolyzing methyl esters having carboxylic acid moieties containing 6 to 22 carbon atoms involves reacting said esters with water in the presence of carboxylic acid and strong acid catalysts to produce acid corresponding to reactant ester and methanol and driving the reaction toward completion by removing the methanol.

17 Claims, No Drawings

HYDROLYSIS OF METHYL ESTERS

BACKGROUND OF THE INVENTION

This invention relates to the field of converting methyl esters to corresponding acids. More particularly, it relates to an improved strong acid process for hydrolyzing methyl esters having carboxylic acid moieties containing 6 to 22 carbon atoms.

It is known that these methyl esters can be hydrolyzed by reacting with water under conditions of high pressure and temperature (e.g. 700 psi and 250° C.). This requires very expensive equipment and presents a methanol flammability problem.

As a result, consideration has been given to converting such esters to acids by an acidolysis reaction wherein an ester of a first carboxylic acid is reacted with a second carboxylic acid in the presence of strong acid catalyst to produce the first carboxylic acid and the ester of the second carboxylic acid. This is a well known reaction and is described, for example, in Graves U.S. Pat. No. 1,882,808. Very often, the acidolysis is an acetolysis, that is, the replacing (displacing) acid is acetic acid. In the context of methyl esters of $C_6$–$C_{22}$ carboxylic acids, this means reacting such ester with acetic acid to produce $C_6$–$C_{22}$ carboxylic acids and methyl acetate. This reaction has the disadvantage in a commercial context of requiring disposal or separate hydrolysis of methyl acetate. Disposal is disadvantageous because consumed displacing acid is lost. Separate hydrolysis has the disadvantage of requiring a second process facility (a reactor and distillation units different from the reactor and distillation units used for the acetolysis) and also the drying of the resulting acetic acid before it can be reused.

It is an object of this invention to provide hydrolysis of the said methyl esters wherein relatively mild conditions of temperature and pressure can be used.

It is a further object of this invention to provide a process wherein displacing acid is not consumed, where no product ester need be disposed of, and where only a single reaction system (e.g. reaction vessel plus distillation means) is required.

DESCRIPTION OF THE INVENTION

It has been discovered that these objects and others are satisfied and various advantages as indicated below are obtained by this invention which involves an overall reaction comprising hydrolyzing methyl ester by reacting such with water in the presence of catalyst consisting essentially of particular carboxylic acid and strong acid to produce carboxylic acid corresponding to the ester and methanol and also involves driving this overall reaction toward completion by removing methanol product from the reaction system (the reaction zones and any fractionation zone as described hereafter).

The overall reaction has the following reaction equation:

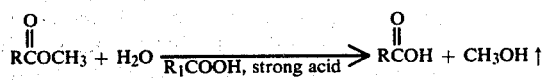

wherein

is methyl ester and R is selected from the group consisting of saturated and unsaturated aliphatic (the ester is described in more detail below; R is used with the same meaning each time it occurs and is described in more detail below) and wherein $R_1COOH$ is carboxylic acid and $R_1$ is an alkyl chain containing from 2 to 4 carbon atoms ($R_1$ is used with the same meaning each time it occurs).

The overall reaction is believed to occur by a two step route. The reaction of the first step is an acidolysis reaction and has the following reaction equation:

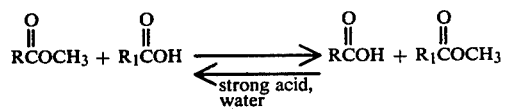

The reaction of the second step is a hydrolysis reaction and has the following reaction equation:

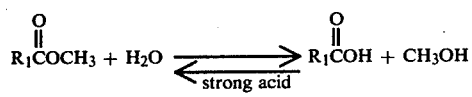

Arrows in both directions are depicted in the above two equations to indicate the capability for reversibility. The process of this invention drives the reactions to the right completely if methanol removal is total.

The overall reaction is readily carried out in a single reaction system e.g. a batch or continuous reactor coupled with distillation means, which provides a liquid phase reaction zone, a vapor phase reaction zone, and a fractionation zone. When the overall reaction is carried out in a reactor coupled with distillation means, the liquid phase reaction zone is provided in the reactor, the vapor phase reaction zone is provided partly in the reactor and partly in the distillation means and the fractionation zone is provided in the distillation means, and the following occurs: The second reaction step occurs in the vapor phase reaction zone, that is, partly in the reactor and partly in the distillation means. Methanol is removed from the fractionation zone to drive the second reaction step toward the right, thereby, in turn, driving the first reaction step toward the right. The $R_1COOH$ formed in the second reaction step is preferably caused to return to the liquid phase reaction zone so that the amount of $R_1COOH$ in that reaction zone stays approximately constant and thereby progressively provides an increased driving force to the right for the acidolysis step (the first reaction step) as methyl ester is converted; this is in contrast to acetolysis where the driving force lessens as the reaction proceeds since acetic acid is used up.

Substitution of acetic acid or formic acid for the $R_1COOH$ does not provide the advantageous results described, and instead, with the aforedescribed single reaction system provides methyl formate or methyl acetate distilling off rather than methanol. These (methyl formate or methyl acetate), contrary to $R_1COOCH_3$, have lower boiling points than methanol and consequently are distilled off instead of methanol requiring new displacing acid and displacing acid ester disposal or hydrolysis of the displacing acid ester in a second process facility (reactor plus distillation means).

We turn now to the methyl ester reactant which as indicated above has the formula RCOOCH$_3$ wherein R is selected from the group consisting of saturated and unsaturated aliphatic chains. The methyl ester has a carboxylic acid moiety containing from 6 to 22 carbon atoms; thus, R contains from 5 to 21 carbon atoms. Examples of suitable methyl esters include methyl caproate, methyl caprylate, methyl caprate, methyl laurate, methyl myristate, methyl myristoleate, methyl palmitate, methyl palmitoleate, methyl stearate, methyl oleate, methyl elaidate, methyl linoleate, methyl linolenate, methyl arachidate, methyl gadoleate, methyl arachidonate, methyl behenate, and methyl erucate. Suitable methyl esters are readily derived from fats and oils (for example, by a methanolysis reaction wherein refined fat or oil is reacted with excess methanol in the presence of sodium methoxide) such as coconut oil, corn oil, cottonseed oil, lard, linseed oil, olive oil, palm oil, palm kernel oil, peanut oil, rapeseed oil, safflower oil, sesame oil, soybean oil, sunflower oil and tallow; in such case, the methyl ester derived from the fat or oil is a mixture of methyl esters. Thus, the methyl ester reactant herein can be a specific methyl ester or a mixture of different methyl esters.

We turn now to the water reactant. The water in the acidolysis reaction step serves as a promoter for the strong acid catalyst (it enhances the strong acid's catalytic activity) and thus acts to speed the reaction. This promoting effect is described in articles by Meade et al at pages 1-6 of volume 39 of Journal of the American Oil Chemists' Society (January 1962). The water also participates as a reactant (see the overall reaction equation and the second reaction step). In general, the water is used in an amount such that the molar ratio of water to methyl ester ranges from about 1:1 to about 25:1. Preferably, the molar ratio of water to methyl ester ranges from about 1.1:1 to about 17.5:1. If a molar ratio less than about 1:1 is utilized, the completeness of the reaction is deleteriously affected or the reaction rate is slowed. If a molar ratio of greater than about 25:1 is utilized, the disadvantage of dilution of the system (resulting in slowing of the reaction) can occur.

Turning now to the carboxylic acid catalyst, as indicated above, it has the formula R$_1$COOH wherein R$_1$ is an alkyl chain containing from 2 to 4 carbon atoms. Thus, the carboxylic acid catalyst is selected from the group consisting of propionic acid, butyric acid, valeric acid and mixtures thereof. Propionic acid has a significant advantage over the others from the standpoints of cost, availability and odor and is therefore highly preferred. As indicated above, the carboxylic acid catalyst participates in the reaction (see the reaction equation of the first reaction step set forth above). It is referred to herein as a catalyst because it is not consumed and because it promotes the overall reaction and thus meets the traditional definition of a catalyst. Initially, it functions to drive the acidolysis step to the right and to compatibilize the reaction mixture. It is used in an amount such that molar ratio of carboxylic acid catalyst to methyl ester ranges from about 1:1 to about 20:1, preferably from about 5:1 to about 17.5:1. If the lower limit of about 1:1 is not met, the reaction rate is slowed. If no carboxylic acid catalyst is used, the overall hydrolysis reaction takes days or stringent conditions of temperature and pressures as described above are necessary. If the upper limit of about 20:1 is exceeded, the disadvantage of separating and/or moving a large volume of carboxylic acid catalyst to reuse it, can occur.

The strong acid catalyst can be, for example, any of those known for use to catalyze acidolysis reactions. The acids can be inorganic or organic, but are not carboxylic. Suitable inorganic acids are those having pK$_a$ values below about 4.0 at room temperature in aqueous solution (see Moeller, *Inorganic Chemistry*, John Wiley & Sons (1952) at pages 314 and 315). Specific examples of such acids are sulfuric acid which is a preferred strong acid catalyst and hydrochloric acid, perchloric acid, nitric acid, phosphoric acid, and hydrofluoric acid. Organic acids suitable for strong acid catalysts herein are noncarboxylic acids having pK$_a$ values below 2.0 in water at room temperature (see *Handbook of Chemistry and Physics*, 58th edition, Chemical Rubber Publishing Company at pages D-150 et seq.). Examples of suitable organic acids are methane sulfonic acid, naphthalene sulfonic acid, trifluoromethyl sulfonic acid, and p-toluene sulfonic acid. Solid strong acids such as strong acid cation exchange resins of the gel or macroreticular types (e.g., Amberlite IR 120, Amberlyst 15, and XN1010, all available from Rohm and Haas), and supported transition metal catalysts as described in U.S. Pat. No. 4,032,550 can also be employed. Mixtures of strong acid catalysts can be used. When a liquid strong acid catalyst is used, the amount of it used generally ranges from about 1% to about 50% by weight of ester reactant, and preferably ranges from about 3.5% to about 20% by weight of ester reactant. A very preferable liquid catalyst is sulfuric acid used in an amount ranging from about 3.5 to about 20% by weight of ester reactant. When a solid strong acid catalyst such as a strong acid cation exchange resin is used, the amount used generally ranges from about 20 to about 120 grams per mole of ester reactant and preferably ranges from about 40 to about 70 grams per mole of ester reactant. If the general lower limits on strong acid catalyst set forth above are not complied with, reaction rate is slowed. If the general upper limits on strong acid catalyst set forth above are exceeded, the disadvantages include increased recycling needs, increased cost, excessive discoloration, and increased occurrence of side reactions. When the reaction is carried out in a reactor coupled with a distillation means as described above, the strong acid catalyst is preferably used in both liquid phase and vapor phase reaction zones; if the reaction is also carried out on a batch basis, it is preferred to use strong acid catalyst in the liquid phase reaction zone in the reactor in a preferred amount as recited above (about 3.5% to about 20% by weight of ester reactant for a liquid strong acid catalyst and about 40 to about 70 grams per mole of ester reactant for solid strong acid catalyst), and strong acid catalyst comprising strong acid cation exchange resin in the vapor phase reaction zone in the distillation means in an amount ranging, for example, from about 10 grams to about 40 grams per 100 gram charge of ester reactant.

Generally, reaction temperatures ranging from about 90° C. to about 140° C. are utilized and very preferably the relatively mild reaction temperatures ranging from about 105° C. to about 125° C. are utilized. The temperature should be sufficient so that methanol can be removed to drive the overall reaction toward completion. When a reactor coupled with a distillation means is the reaction system, and the reaction is carried out at about atmospheric pressure and propionic acid is the carboxylic acid catalyst, the temperature is preferably adjusted so that the temperature at the outlet of the fractionation zone is about 65° C. which is the boiling point of methanol at atmospheric pressure or so that the temperature at the outlet of the fractionation zone is sufficient for separation of methanol from methyl propionate (below 80° C.).

The overall reaction is readily and preferably carried out at atmospheric pressure. If desired, subatmospheric or superatmospheric pressures can be utilized.

The time for reaction is dependent on several factors. Generally, increasing amounts of water, carboxylic acid catalyst and/or strong acid catalyst increase reaction rate. In general, in batch processing, relatively high percentage conversions (50–100%) are readily obtained in about one to four hours. In continuous processing, residence times are chosen for a particular combination of reaction parameters so as to obtain high percentage conversions.

Carboxylic acid product is readily obtained from a resultant reaction mixture as follows. If such resultant reaction mixture is heterogeneous, the layer containing such product is, for example, separated, washed and distilled or fractionally crystallized for final purification. If a resultant reaction mixture is homogeneous, the carboxylic acid product is readily recovered by adding sufficient water to form a heterogeneous mixture and proceeding as for a heterogeneous mixture. Any carboxylic acid catalyst or strong acid recovered by layering or washing or filtration (if the strong acid is a solid) is readily recycled. Methanol which is recovered during the reaction can be used for methanolysis of triglycerides to obtain methyl ester reactant.

As indicated above, the process of this invention is readily carried out batchwise or continuously. When the process is a batch process, the amounts specified above are those used, that is introduced, into the batch reactor system. When the process is continuous, the amounts specified above are those maintained. For a batch process suitable equipment includes a reaction vessel or pot containing the reactants and catalysts communicating with a fractionation column thereabove containing at its lower end strong acid cation exchange resin. For a continuous reaction, the reactor can be, for example, the same as the batch reactor but containing means for continuous addition of reactants and continuous removal of fatty acid and methanol.

The term "fatty acid" is used herein to mean carboxylic acid corresponding to carboxylic acid moiety in ester reactant.

The invention is illustrated by the following specific examples.

EXAMPLE I

Methyl laurate (Procter & Gamble Company Stock No. CE 1295; 95% minimum $C_{12}$ methyl esters, 82.9 grams, 0.39 moles), propionic acid (151.6 grams, 2.05 moles), water (9.4 grams, 0.52 moles) and concentrated sulfuric acid (3.7 grams, 0.04 moles) were placed in a mantle-heated flask connected to a 30 cm. distillation column and take-off head. The bottom one-fourth of the distillation column was packed with Amberlite IR 120 (obtained from Rohm & Haas Co.) ion exchange resin in the acid form (about 10 grams of strong acid cation exchange resin). The flask was heated for two hours with the contents holding at 117°–118° C. until the end of the reaction when the temperature reached 151° C. Methanol was taken off at the head during the reaction. Methanol taken off corresponded to a 97.6% conversion to lauric acid indicating very high reaction completeness.

EXAMPLE II

Methyl laurate (same feedstock as Example I, 87.1 grams, 0.41 moles), propionic acid (207.3 grams, 2.8 moles), water (25.2 grams, 1.4 moles) and Amberlyst 15 (strong acid macroreticular cation exchange resin obtained from Rohm & Haas, 24.0 grams dry weight) in the acid form were added as described below to a round bottom flask equipped with 30 cm. distillation column (attached to a fractionating take-off head) having the bottom 8 cm. packed with methanol soaked Amberlyst 15 (about 10 grams). The Amberlyst 15 added to the flask was previously soaked in methyl laurate for 21 hours, filtered, and then added to the methyl laurate reactant already in the flask. This was heated to 100° C. The propionic acid and water were heated to 80° C. and then added to the ester and Amberlyst 15 already in the flask. Heat was applied to the flask via a heating mantle and the pot temperature reached 96° C. when methanol collection began. In two hours of heating, methanol collection continued and the pot temperature gradually increased to 132° C. At this time, 10.5 milliliters of methanol was collected, representing 61.3% of theoretical yield and indicating over 50% conversion of methyl laurate to lauric acid.

EXAMPLE III

Methyl laurate (same feedstock as in Example I, 84.6 grams, 0.40 moles), propionic acid (210.2 grams, 2.84 moles), water (25.4 grams, 1.4 moles) and XN1010 (Rohm & Haas Co. experimental macroreticular resin of the polystyrene sulfonic acid type, having an ion exchange capacity of 3.3 meq/gram and a surface area of 570 $m^2$/gram, 24.2 grams dry weight) were added as described below to a mantle-heated flask equipped with a 30 cm. distillation column (the bottom 8 cm. of which were packed with methanol soaked XN1010 in an amount of about 10 grams) attached to a fractionating take-off head. The XN1010 catalyst was previously soaked in methyl laurate for 21 hours, filtered, added to the methyl laurate reactant and heated to 100° C. The propionic acid and water were mixed, heated to 80° C. and added to the flask. Heat was applied to the flask, and the contents reached a maximum of 121° C. over a 65 minute heating period. Methanol was taken off at the head during the reaction. Work-up of the product and isolation of lauric acid gave a 91.1% yield.

EXAMPLE IV

Methyl oleate (100 grams, 0.338 moles), propionic acid (400.4 grams, 5.4 moles), water (50 grams, 2.8 moles) and concentrated sulfuric acid (20 grams, 0.2 moles) were placed in a mantle-heated flask connected to a 30 cm. distillation column (the bottom 8 cm. of which were packed with approximately 10 grams of strong acid cation exchange resin) attached to a take-off head. The flask was heated for two hours to provide a reaction temperature of approximately 105° C. Methanol was collected at the take-off head during the reaction. Analysis indicated 98% conversion to oleic acid.

EXAMPLE V

Methyl oleate (100 grams, 0.338 moles), propionic acid (250.3 grams, 3.38 moles), concentrated sulfuric acid (12 grams, 0.12 moles), distilled water (100 grams, 5.56 moles), and Covi-Ox T-50 antioxidant (0.087 grams) are charged to a mantle-heated round bottom flask connected to a 30 cm. distillation column fitted with a take-off head. The bottom 8 cm. of the distillation column is packed with approximately 10 grams of XN1010 ion exchange resin (described in Example III) in pellet form. The distillation column is designed to allow vapor flow upward through the resin packing but liquid downflow is returned without passing through the resin packing. The flask is heated to between 105° C. and 110° C. for three hours. Methanol is taken off at the take-off head during reaction. Sample workup and analysis indicates a 99% yield of oleic acid.

EXAMPLE VI

Coconut-derived methyl esters (CE810, Procter & Gamble Company; typical analysis: 3.9% $C_6$, 56.2% $C_8$, 39.2% $C_{10}$, 0.7% $C_{12}$; 50 grams; (0.3 moles), propionic acid (110.9 grams, 1.5 moles), concentrated sulfuric acid (2 grams, 0.02 moles), and water (6 grams, 0.33 moles) were placed in a mantle-heated flask connected to a 30 cm. distillation column (the bottom 8 cm. of which were packed with approximately 10 grams of strong acid cation exchange resin) fitted with a take-off head. The flask was heated for 2 hours to provide a reaction temperature of approximately 110° C. Methanol was collected at the take-off head during the reaction. Analysis indicated 91% conversion to fatty acids.

EXAMPLE VII

Example VI was repeated except that the amounts were as follows: Coconut-derived methyl esters (CE810), 100 grams, 0.6 moles; propionic acid (354.9 grams, 4.8 moles); concentrated sulfuric acid (10 grams, 0.1 moles); and water (12 grams, 0.67 moles). Analysis indicated 94% conversion to fatty acids.

EXAMPLE VIII

Coconut-derived methyl esters (CE810, Procter & Gamble Company, described in Example VI, 100 grams, 0.6 moles), propionic acid (354.9 grams, 4.8 moles) concentrated sulfuric acid (4 grams, 0.04 moles) and distilled water (20 grams, 1.11 moles) are charged to a mantle-heated, round bottom flask connected to a 30 cm. distillation column fitted with a take-off head. The bottom 8 cm. of the distillation column is packed with approximately 10 grams of XN1010 ion exchange resin (described in Example III) in pellet form. The distillation column is designed to allow vapor flow through the resin packing but liquid downflow is returned without passing through the resin packing. The flask is heated up to 120° C. Heat is applied for two hours. Methanol is taken off at the take-off head during the reaction. Sample workup and analysis shows a 97.7% yield of the fatty acids.

EXAMPLE IX

Methyl linoleate (50 grams, 0.17 moles), propionic acid (175.8 grams, 2.37 moles), concentrated sulfuric acid (6 grams, 0.06 moles) and water (30 grams, 1.66 moles) were placed in a mantle-heated flask connected to a 30 cm. distillation column (the bottom 8 cm. of which were packed with approximately 10 grams of strong acid cation exchange resin) fitted with a take-off head. The flask was heated for three hours to provide a reaction temperature of approximately 105° C. Methanol was collected at the take-off head during the reaction. Analysis indicated 98% conversion to linoleic acid.

EXAMPLE X

Safflower methyl esters (50 grams, 0.17 moles), propionic acid (126 grams, 1.7 moles), p-toluene sulfonic acid (20.6 grams, 0.12 moles) and water (3.6 grams, 1.9 moles) were placed in a mantle-heated flask connected to a 30 cm. distillation column (the bottom 8 cm. of which were packed with approximately 10 grams of strong acid cation exchange resin) fitted with a take-off head. The flask was heated for 3 hours to provide a reaction temperature of approximately 105° C. Methanol was collected at the take-off head during the reaction. Analysis indicated 99.3% conversion to safflower fatty acids.

In the above examples the portion of the distillation column packed with resin constitutes vapor phase reaction zone.

When in the above examples, equivalent amounts of butyric acid, or valeric acid are substituted for part of or all the propionic acid, substantially equal yields and conversions are obtained.

While the foregoing describes preferred embodiments of the invention, modifications will be readily apparent to those skilled in the art. The scope of the invention is intended to be defined by the following claims.

What is claimed is:

1. A process for hydrolyzing methyl ester having a carboxylic acid moiety containing from 6 to 22 carbon atoms, said process comprising
   (a) reacting said ester with water in the presence of catalyst consisting essentially of carboxylic acid catalyst and strong acid to produce carboxylic acid corresponding to said ester and methanol; said water being utilized in an amount such that the molar ratio of water to methyl ester is at least about 1:1; said carboxylic acid catalyst being selected from the group consisting of propionic acid, butyric acid, valeric acid and mixtures thereof; and
   (b) driving the reaction toward completion by removing methanol.

2. A process as recited in claim 1 in which the carboxylic acid catalyst is propionic acid.

3. A process as recited in claim 2, in which the molar ratio of water to methyl ester ranges from about 1:1 to about 25:1.

4. A process as recited in claim 3, in which the molar ratio of water to methyl ester ranges from about 1.1:1 to about 17.5:1.

5. A process as recited in claim 2, in which the molar ratio of propionic acid to methyl ester ranges from about 1:1 to about 20:1.

6. A process as recited in claim 2, in which the molar ratio of propionic acid to methyl ester is at least about 1:1.

7. A process as recited in claim 5, in which the molar ratio of propionic acid to methyl ester ranges from about 5:1 to about 17.5:1.

8. A process as recited in claim 2, in which said strong acid comprises liquid used in an amount ranging from about 1% to about 50% by weight of said methyl ester.

9. A process as recited in claim 8, in which said strong acid comprises sulfuric acid in an amount ranging from about 3.5% to about 25% by weight of said methyl ester.

10. A process as recited in claim 2, in which said strong acid comprises strong acid cation exchange resin used in an amount ranging from about 20 to about 120 grams per mole of methyl ester.

11. A process as recited in claim 10, in which said strong acid comprises strong acid cation exchange resin used in an amount ranging from about 40 to 70 grams per mole of methyl ester.

12. A process as recited in claim 2, in which the reaction is carried out in a liquid phase reaction zone and a vapor phase reaction zone.

13. A process as recited in claim 12, in which strong acid catalyst comprising sulfuric acid is used in said liquid phase reaction zone in an amount ranging from about 3.5% to about 20% by weight of methyl ester and strong acid catalyst comprising strong acid cation exchange resin is used in said vapor phase reaction zone in an amount ranging from about 10 to about 40 grams per 100 gram charge of methyl ester.

14. A process as recited in claim 12, in which the molar ratio of water to methyl ester ranges from about 1:1 to about 25:1 and the molar ratio of propionic acid to methyl ester ranges from about 1:1 to about 20:1.

15. A process as recited in claim 14, in which the molar ratio of water to methyl ester ranges from about 1.1:1 to about 17.5:1, in which the molar ratio of propionic acid to methyl ester ranges from about 5:1 to about 17.5:1.

16. A process as recited in claim 15, in which the methyl ester has the formula $RCOOCH_3$ in which R is selected from the group consisting of saturated and unsaturated aliphatic chains.

17. A process as defined in claim 15, in which the methyl ester is a mixture of different methyl esters.

* * * * *